United States Patent
Honma et al.

(10) Patent No.: US 10,065,975 B2
(45) Date of Patent: Sep. 4, 2018

(54) AMINO-CONTAINING ORGANOSILICON COMPOUND AND MAKING METHOD

(71) Applicant: Shin-Etsu Chemical Co., Ltd., Tokyo (JP)

(72) Inventors: Takayuki Honma, Joetsu (JP); Tohru Kubota, Joetsu (JP); Yoichi Tonomura, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/200,132

(22) Filed: Jul. 1, 2016

(65) Prior Publication Data

US 2017/0002030 A1 Jan. 5, 2017

(30) Foreign Application Priority Data

Jul. 3, 2015 (JP) .................................. 2015-134132

(51) Int. Cl.
C07F 7/04 (2006.01)
C07F 7/18 (2006.01)
C08K 5/54 (2006.01)

(52) U.S. Cl.
CPC ............ *C07F 7/1812* (2013.01); *C07F 7/184* (2013.01); *C07F 7/1836* (2013.01); *C08K 5/54* (2013.01)

(58) Field of Classification Search
CPC ........... C07F 7/1836; C07F 7/184; C08K 5/54
USPC ....................................................... 556/413
See application file for complete search history.

(56) References Cited

U.S. PATENT DOCUMENTS

| | | | |
|---|---|---|---|
| 5,282,998 A | 2/1994 | Horn et al. | |
| 6,841,197 B2 | 1/2005 | Standke et al. | |
| 8,013,178 B2 | 9/2011 | Klockmann et al. | |
| 8,049,027 B2 * | 11/2011 | Honma | C07F 7/184 544/229 |
| 2010/0234502 A1 * | 9/2010 | Iwasaki | C07F 7/1836 524/188 |
| 2016/0326274 A1 | 11/2016 | Sakurai et al. | |

FOREIGN PATENT DOCUMENTS

| | | |
|---|---|---|
| JP | 2962934 B2 | 10/1999 |
| JP | 2002-226490 A | 8/2002 |
| JP | 2006-249069 A | 9/2006 |
| JP | 5359585 B2 | 12/2013 |
| WO | WO 2015/098264 A1 | 7/2015 |

* cited by examiner

*Primary Examiner* — Clinton Brooks
*Assistant Examiner* — Kofi Adamli
(74) *Attorney, Agent, or Firm* — Birch, Stewart, Kolasch & Birch, LLP (57) ABSTRACT

An amino-containing organosilicon compound having formula (1) is used for surface treatment of an inorganic filler for thereby rendering the filler more compatible with and adhesive to a polymer material. In formula (1), $R^1$ is alkyl, alkenyl, aryl or aralkyl, $R^2$ is alkenyl, aryl or aralkyl, $R^3$ and $R^4$ each are a monovalent hydrocarbon group, and n is 0, 1 or 2.

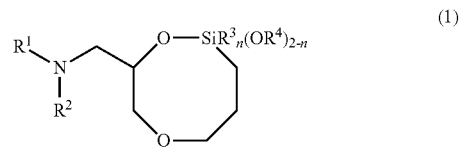

7 Claims, 6 Drawing Sheets

AMINO-CONTAINING ORGANOSILICON COMPOUND AND MAKING METHOD

CROSS-REFERENCE TO RELATED APPLICATION

This non-provisional application claims priority under 35 U.S.C. § 119(a) on Patent Application No. 2015-134132 filed in Japan on Jul. 3, 2015, the entire contents of which are hereby incorporated by reference.

TECHNICAL FIELD

This invention relates to amino-containing organosilicon compounds which are useful as silane coupling agents, surface treating agents, textile treating agents, adhesives, paint additives, and polymer modifiers, and a method for preparing the same.

BACKGROUND ART

It is well known in the art that organosilicon compounds containing an amino group are useful as silane coupling agents, surface treating agents, textile treating agents, adhesives, paint additives and the like. Specifically, when an inorganic material such as glass fiber, metal or oxide filler is added to a polymer material for the purpose of improving mechanical properties and heat resistance, the adhesion between the polymer material and the inorganic material and the dispersion of the inorganic material in the polymer material are improved using the amino-containing organosilicon compound. The effect of adding the inorganic material is enhanced beyond expectation.

As is also known in the art, silane coupling agents such as the above organosilicon compounds generate a considerable amount of alcohol on use, typically during mixing step. In conjunction with environmental issues associated with global warming and health problems, the recent challenge is a reduction of volatile organic compounds (VOC). Efforts have been made to achieve a saving of VOC by reducing the amount of alcohol generated from silane coupling agents. For example, the amount of alcohol generated on use is reduced by partly replacing an alkoxy group of an alkoxysilane by a nonvolatile long-chain alkyl polyether group as described in JP-A 2006-249069 or by subjecting an alkoxysilane to partial hydrolytic condensation to form a siloxane oligomer having some alkoxy groups left intact as described in JP 2962934 and JP-A 2002-226490.

These organosilicon compounds intended to reduce alcohol generation, that is, silanes having a nonvolatile group replaced or oligomers obtained by forming an intermolecular siloxane bond and having a relatively high molecular weight are difficult to purify by distillation. Few target compounds are of high purity. Since the target compound is available as a mixture, the physical properties are inconsistent. To overcome these drawbacks, JP 5359585 discloses an amino-containing organosilicon compound which can be readily purified and generates a less amount of alcohol during use.

CITATION LIST

Patent Document 1: JP-A 2006-249069 (U.S. Pat. No. 8,013,178)
Patent Document 2: JP 2962934 (U.S. Pat. No. 5,282,998)
Patent Document 3: JP-A 2002-226490 (U.S. Pat. No. 6,841,197)
Patent Document 4: JP 5359585 (U.S. Pat. No. 8,049,027)

DISCLOSURE OF INVENTION

The organosilicon compounds designed to generate a less amount of alcohol have the problem that when the organosilicon compound is used for surface treatment of an inorganic material, the treated inorganic material is still insufficient in compatibility with and adhesion to resins. Further improvements in these properties are desired.

There is a desire to have an amino-containing organosilicon compound which is easy to purify, generates a less amount of alcohol during use, and is used for surface treatment of an inorganic material for thereby rendering the treated inorganic material more compatible with and adhesive to resins.

An object of the invention is to provide an amino-containing organosilicon compound which is easy to purify, generates a less amount of alcohol during use, and is used for surface treatment of an inorganic material for thereby rendering the treated inorganic material more compatible with and adhesive to resins. Another object is to provide a method for preparing the same.

In one aspect, the invention provides an amino-containing organosilicon compound having the general formula (1).

Herein $R^1$ is a substituted or unsubstituted, $C_1$-$C_{10}$ alkyl, $C_2$-$C_{10}$ alkenyl, $C_6$-$C_{10}$ aryl or $C_7$-$C_{10}$ aralkyl group, $R^2$ is a substituted or unsubstituted, $C_2$-$C_{10}$ alkenyl, $C_6$-$C_{10}$ aryl or $C_7$-$C_{10}$ aralkyl group, $R^3$ and $R^4$ are each independently a substituted or unsubstituted, $C_1$-$C_{10}$ monovalent hydrocarbon group, and n is an integer of 0 to 2.

In another aspect, the invention provides a method for preparing the amino-containing organosilicon compound, comprising the steps of reacting an amine compound with a γ-glycidoxypropylalkoxysilane, and subjecting the resulting reaction mixture to dealcoholization cyclization under solvent reflux, the amine compound having the general formula (2):

wherein $R^1$ is a substituted or unsubstituted, $C_1$-$C_{10}$ alkyl, $C_2$-$C_{10}$ alkenyl, $C_6$-$C_{10}$ aryl or $C_7$-$C_{10}$ aralkyl group and $R^2$ is a substituted or unsubstituted, $C_2$-$C_{10}$ alkenyl, $C_6$-$C_{10}$ aryl or $C_7$-$C_{10}$ aralkyl group, and the γ-glycidoxypropylalkoxysilane having the general formula (3):

wherein $R^3$ and $R^4$ are each independently a substituted or unsubstituted, $C_1$-$C_{10}$ monovalent hydrocarbon group, and n is an integer of 0 to 2.

In a further aspect, the invention provides a method for preparing the amino-containing organosilicon compound, comprising the step of reacting an amine compound having formula (2) with a γ-glycidoxypropylalkoxysilane having formula (3) while simultaneously effecting dealcoholization cyclization under solvent reflux.

In a preferred embodiment, the dealcoholization cyclization is effected in the presence of a basic catalyst.

Advantageous Effects of Invention

The amino-containing organosilicon compound of the invention is used for surface treatment of an inorganic material for thereby rendering the treated inorganic material more compatible with and adhesive to polymer materials and hence, endowing the polymer materials with improved mechanical properties and heat resistance. The organosilicon compound is easy to purify, and generates a less amount of alcohol on use. The organosilicon compound which is free of active hydrogen atoms may be added to compositions based on polymers having active hydrogen-reactive functional groups such as isocyanate and epoxy groups, because the functional groups undergo no reaction. On use of the amino-containing organosilicon compound, only hydroxyl groups may be generated via hydrolysis or the like. When the organosilicon compound is used as a terminal modifier for anionic polymerization, anionic polymerization terminals selectively react with alkoxy silicon sites, but not with the endocyclic oxygen on the organosilicon compound. Then silicon-bonded oxygen atoms are quantitatively introduced at anionic polymerization terminals. On subsequent hydrolysis, an amino and hydroxyl-modified polymer is readily prepared.

DESCRIPTION OF PREFERRED EMBODIMENT

The notation (Cn-Cm) means a group containing from n to m carbon atoms per group.

The invention provides an amino-containing organosilicon compound having the general formula (1).

(1)

Herein $R^1$ is a substituted or unsubstituted, $C_1$-$C_{10}$ alkyl, $C_2$-$C_{10}$ alkenyl, $C_6$-$C_{10}$ aryl or $C_7$-$C_{10}$ aralkyl group. $R^2$ is a substituted or unsubstituted, $C_2$-$C_{10}$ alkenyl, $C_6$-$C_{10}$ aryl or $C_7$-$C_{10}$ aralkyl group. $R^3$ and $R^4$ are each independently a substituted or unsubstituted, $C_1$-$C_{10}$ monovalent hydrocarbon group, and n is an integer of 0 to 2.

In formula (1), $R^1$ is a substituted or unsubstituted alkyl group of 1 to 10 carbon atoms, preferably 1 to 6 carbon atoms, a substituted or unsubstituted alkenyl group of 2 to 10 carbon atoms, preferably 2 to 6 carbon atoms, a substituted or unsubstituted $C_6$-$C_{10}$ aryl group, or a substituted or unsubstituted $C_7$-$C_{10}$ aralkyl group. Illustrative examples include straight alkyl groups such as methyl, ethyl, n-propyl, n-butyl, n-pentyl, n-hexyl, n-heptyl, n-octyl, n-nonyl, n-decyl, n-undecyl and n-dodecyl, branched alkyl groups such as isopropyl, isobutyl, sec-butyl, tert-butyl, isopentyl, neopentyl, isohexyl, isoheptyl, isooctyl, tert-octyl, isononyl, isodecyl, isoundecyl and isododecyl, cyclic alkyl groups such as cyclopentyl and cyclohexyl, alkenyl groups such as vinyl, allyl, methallyl, butenyl, heptenyl, hexenyl and cyclohexenyl, aryl groups such as phenyl, tolyl and xylyl, and aralkyl groups such as benzyl. From the aspect of improving compatibility with resins, vinyl, allyl and phenyl are preferred. Some or all hydrogen atoms on the hydrocarbon group may be substituted. Suitable substituents include alkoxy groups such as methoxy, ethoxy and (iso)propoxy, groups containing halogen such as fluorine, chlorine, bromine and iodine, cyano, amino, aromatic hydrocarbon, ester, alkyl separated by an oxygen atom, acyl, sulfide, alkylsilyl, alkoxysilyl, and mixtures thereof. Neither the site of substitution with such a substituent nor the number of substituents is limited.

In formula (1), $R^2$ is a substituted or unsubstituted alkenyl group of 2 to 10 carbon atoms, preferably 2 to 6 carbon atoms, a substituted or unsubstituted aryl group of 6 to 10 carbon atoms, or a substituted or unsubstituted aralkyl group of 7 to 10 carbon atoms. Illustrative examples include alkenyl groups such as vinyl, allyl, methallyl, butenyl, heptenyl, hexenyl and cyclohexenyl, aryl groups such as phenyl, tolyl and xylyl, and aralkyl groups such as benzyl. From the aspect of improving compatibility with resins, vinyl, allyl and phenyl are preferred. Some or all hydrogen atoms on the hydrocarbon group may be substituted, and suitable substituents are as exemplified above for $R^1$.

In formula (1), $R^3$ and $R^4$ are each independently a substituted or unsubstituted monovalent hydrocarbon group of 1 to 10 carbon atoms, preferably 1 to 6 carbon atoms, examples of which include straight, branched or cyclic alkyl, aryl, and aralkyl groups. Illustrative examples include straight alkyl groups such as methyl, ethyl, n-propyl, n-butyl, n-pentyl, n-hexyl, n-heptyl, n-octyl, n-nonyl, n-decyl, n-undecyl and n-dodecyl, branched alkyl groups such as isopropyl, isobutyl, sec-butyl, tert-butyl, isopentyl, neopentyl, isohexyl, isoheptyl, isooctyl, tert-octyl, isononyl, isodecyl, isoundecyl and isododecyl, cyclic alkyl groups such as cyclopentyl and cyclohexyl, aryl groups such as phenyl, tolyl and xylyl, and aralkyl groups such as benzyl. Some or all hydrogen atoms on the hydrocarbon group may be substituted, and suitable substituents are as exemplified above for $R^1$. From the economical aspect, methyl and ethyl are preferred.

Examples of the compound having formula (1) include:
2,2-dimethoxy-8-(N-methyl-N-vinylaminomethyl)-1,6-dioxa-2-silacyclooctane,
2,2-dimethoxy-8-(N-ethyl-N-vinylaminomethyl)-1,6-dioxa-2-silacyclooctane,
2,2-dimethoxy-8-(N-propyl-N-vinylaminomethyl)-1,6-dioxa-2-silacyclooctane,

2,2-dimethoxy-8-(N-butyl-N-vinylaminomethyl)-1,6-dioxa-2-silacyclooctane,
2,2-dimethoxy-8-(N-isopropyl-N-vinylaminomethyl)-1,6-dioxa-2-silacyclooctane,
2,2-dimethoxy-8-(N-cyclohexyl-N-vinylaminomethyl)-1,6-dioxa-2-silacyclooctane,
2,2-dimethoxy-8-(N,N-divinylaminomethyl)-1,6-dioxa-2-silacyclooctane,
2,2-dimethoxy-8-(N-allyl-N-vinylaminomethyl)-1,6-dioxa-2-silacyclooctane,
2,2-dimethoxy-8-(N-phenyl-N-vinylaminomethyl)-1,6-dioxa-2-silacyclooctane,
2,2-dimethoxy-8-(N-benzyl-N-vinylaminomethyl)-1,6-dioxa-2-silacyclooctane,
2,2-dimethoxy-8-(N-methyl-N-allylaminomethyl)-1,6-dioxa-2-silacyclooctane,
2,2-dimethoxy-8-(N-ethyl-N-allylaminomethyl)-1,6-dioxa-2-silacyclooctane,
2,2-dimethoxy-8-(N-propyl-N-allylaminomethyl)-1,6-dioxa-2-silacyclooctane,
2,2-dimethoxy-8-(N-butyl-N-allylaminomethyl)-1,6-dioxa-2-silacyclooctane,
2,2-dimethoxy-8-(N-isopropyl-N-allylaminomethyl)-1,6-dioxa-2-silacyclooctane,
2,2-dimethoxy-8-(N-cyclohexyl-N-allylaminomethyl)-1,6-dioxa-2-silacyclooctane,
2,2-dimethoxy-8-(N,N-diallylaminomethyl)-1,6-dioxa-2-silacyclooctane,
2,2-dimethoxy-8-(N-phenyl-N-allylaminomethyl)-1,6-dioxa-2-silacyclooctane,
2,2-dimethoxy-8-(N-benzyl-N-allylaminomethyl)-1,6-dioxa-2-silacyclooctane,
2,2-dimethoxy-8-(N-methyl-N-phenylaminomethyl)-1,6-dioxa-2-silacyclooctane,
2,2-dimethoxy-8-(N-ethyl-N-phenylaminomethyl)-1,6-dioxa-2-silacyclooctane,
2,2-dimethoxy-8-(N-propyl-N-phenylaminomethyl)-1,6-dioxa-2-silacyclooctane,
2,2-dimethoxy-8-(N-butyl-N-phenylaminomethyl)-1,6-dioxa-2-silacyclooctane,
2,2-dimethoxy-8-(N-isopropyl-N-phenylaminomethyl)-1,6-dioxa-2-silacyclooctane,
2,2-dimethoxy-8-(N-cyclohexyl-N-phenylaminomethyl)-1,6-dioxa-2-silacyclooctane,
2,2-dimethoxy-8-(N,N-diphenylaminomethyl)-1,6-dioxa-2-silacyclooctane,
2,2-dimethoxy-8-(N-allyl-N-phenylaminomethyl)-1,6-dioxa-2-silacyclooctane,
2,2-dimethoxy-8-(N-benzyl-N-phenylaminomethyl)-1,6-dioxa-2-silacyclooctane,
2,2-diethoxy-8-(N-methyl-N-vinylaminomethyl)-1,6-dioxa-2-silacyclooctane,
2,2-diethoxy-8-(N-ethyl-N-vinylaminomethyl)-1,6-dioxa-2-silacyclooctane,
2,2-diethoxy-8-(N-propyl-N-vinylaminomethyl)-1,6-dioxa-2-silacyclooctane,
2,2-diethoxy-8-(N-butyl-N-vinylaminomethyl)-1,6-dioxa-2-silacyclooctane,
2,2-diethoxy-8-(N-isopropyl-N-vinylaminomethyl)-1,6-dioxa-2-silacyclooctane,
2,2-diethoxy-8-(N-cyclohexyl-N-vinylaminomethyl)-1,6-dioxa-2-silacyclooctane,
2,2-diethoxy-8-(N,N-divinylaminomethyl)-1,6-dioxa-2-silacyclooctane,
2,2-diethoxy-8-(N-allyl-N-vinylaminomethyl)-1,6-dioxa-2-silacyclooctane,
2,2-diethoxy-8-(N-phenyl-N-vinylaminomethyl)-1,6-dioxa-2-silacyclooctane,
2,2-diethoxy-8-(N-benzyl-N-vinylaminomethyl)-1,6-dioxa-2-silacyclooctane,
2,2-diethoxy-8-(N-methyl-N-allylaminomethyl)-1,6-dioxa-2-silacyclooctane,
2,2-diethoxy-8-(N-ethyl-N-allylaminomethyl)-1,6-dioxa-2-silacyclooctane,
2,2-diethoxy-8-(N-propyl-N-allylaminomethyl)-1,6-dioxa-2-silacyclooctane,
2,2-diethoxy-8-(N-butyl-N-allylaminomethyl)-1,6-dioxa-2-silacyclooctane,
2,2-diethoxy-8-(N-isopropyl-N-allylaminomethyl)-1,6-dioxa-2-silacyclooctane,
2,2-diethoxy-8-(N-cyclohexyl-N-allylaminomethyl)-1,6-dioxa-2-silacyclooctane,
2,2-diethoxy-8-(N,N-diallylaminomethyl)-1,6-dioxa-2-silacyclooctane,
2,2-diethoxy-8-(N-phenyl-N-allylaminomethyl)-1,6-dioxa-2-silacyclooctane,
2,2-diethoxy-8-(N-benzyl-N-allylaminomethyl)-1,6-dioxa-2-silacyclooctane,
2,2-diethoxy-8-(N-methyl-N-phenylaminomethyl)-1,6-dioxa-2-silacyclooctane,
2,2-diethoxy-8-(N-ethyl-N-phenylaminomethyl)-1,6-dioxa-2-silacyclooctane,
2,2-diethoxy-8-(N-propyl-N-phenylaminomethyl)-1,6-dioxa-2-silacyclooctane,
2,2-diethoxy-8-(N-butyl-N-phenylaminomethyl)-1,6-dioxa-2-silacyclooctane,
2,2-diethoxy-8-(N-isopropyl-N-phenylaminomethyl)-1,6-dioxa-2-silacyclooctane,
2,2-diethoxy-8-(N-cyclohexyl-N-phenylaminomethyl)-1,6-dioxa-2-silacyclooctane,
2,2-diethoxy-8-(N,N-diphenylaminomethyl)-1,6-dioxa-2-silacyclooctane,
2,2-diethoxy-8-(N-allyl-N-phenylaminomethyl)-1,6-dioxa-2-silacyclooctane,
2,2-diethoxy-8-(N-benzyl-N-phenylaminomethyl)-1,6-dioxa-2-silacyclooctane,
2-methoxy-2-methyl-8-(N-methyl-N-vinylaminomethyl)-1,6-dioxa-2-silacyclooctane,
2-methoxy-2-methyl-8-(N-ethyl-N-vinylaminomethyl)-1,6-dioxa-2-silacyclooctane,
2-methoxy-2-methyl-8-(N-propyl-N-vinylaminomethyl)-1,6-dioxa-2-silacyclooctane,
2-methoxy-2-methyl-8-(N-butyl-N-vinylaminomethyl)-1,6-dioxa-2-silacyclooctane,
2-methoxy-2-methyl-8-(N-isopropyl-N-vinylaminomethyl)-1,6-dioxa-2-silacyclooctane,
2-methoxy-2-methyl-8-(N-cyclohexyl-N-vinylaminomethyl)-1,6-dioxa-2-silacyclooctane,
2-methoxy-2-methyl-8-(N,N-divinylaminomethyl)-1,6-dioxa-2-silacyclooctane,
2-methoxy-2-methyl-8-(N-allyl-N-vinylaminomethyl)-1,6-dioxa-2-silacyclooctane,
2-methoxy-2-methyl-8-(N-phenyl-N-vinylaminomethyl)-1,6-dioxa-2-silacyclooctane,
2-methoxy-2-methyl-8-(N-benzyl-N-vinylaminomethyl)-1,6-dioxa-2-silacyclooctane,
2-methoxy-2-methyl-8-(N-methyl-N-allylaminomethyl)-1,6-dioxa-2-silacyclooctane,
2-methoxy-2-methyl-8-(N-ethyl-N-allylaminomethyl)-1,6-dioxa-2-silacyclooctane,
2-methoxy-2-methyl-8-(N-propyl-N-allylaminomethyl)-1,6-dioxa-2-silacyclooctane, 2-methoxy-2-methyl-8-(N-butyl-N-allylaminomethyl)-1,6-dioxa-2-silacyclooctane,
2-methoxy-2-methyl-8-(N-isopropyl-N-allylaminomethyl)-1,6-dioxa-2-silacyclooctane,
2-methoxy-2-methyl-8-(N-cyclohexyl-N-allylaminomethyl)-1,6-dioxa-2-silacyclooctane,
2-methoxy-2-methyl-8-(N,N-diallylaminomethyl)-1,6-dioxa-2-silacyclooctane,
2-methoxy-2-methyl-8-(N-phenyl-N-allylaminomethyl)-1,6-dioxa-2-silacyclooctane,
2-methoxy-2-methyl-8-(N-benzyl-N-allylaminomethyl)-1,6-dioxa-2-silacyclooctane,
2-methoxy-2-methyl-8-(N-methyl-N-phenylaminomethyl)-1,6-dioxa-2-silacyclooctane,
2-methoxy-2-methyl-8-(N-ethyl-N-phenylaminomethyl)-1,6-dioxa-2-silacyclooctane,
2-methoxy-2-methyl-8-(N-propyl-N-phenylaminomethyl)-1,6-dioxa-2-silacyclooctane,
2-methoxy-2-methyl-8-(N-butyl-N-phenylaminomethyl)-1,6-dioxa-2-silacyclooctane,
2-methoxy-2-methyl-8-(N-isopropyl-N-phenylaminomethyl)-1,6-dioxa-2-silacyclooctane,
2-methoxy-2-methyl-8-(N-cyclohexyl-N-phenylaminomethyl)-1,6-dioxa-2-silacyclooctane,
2-methoxy-2-methyl-8-(N,N-diphenylaminomethyl)-1,6-dioxa-2-silacyclooctane,
2-methoxy-2-methyl-8-(N-allyl-N-phenylaminomethyl)-1,6-dioxa-2-silacyclooctane,
2-methoxy-2-methyl-8-(N-benzyl-N-phenylaminomethyl)-1,6-dioxa-2-silacyclooctane,
2-ethoxy-2-methyl-8-(N-methyl-N-vinylaminomethyl)-1,6-dioxa-2-silacyclooctane,
2-ethoxy-2-methyl-8-(N-ethyl-N-vinylaminomethyl)-1,6-dioxa-2-silacyclooctane,
2-ethoxy-2-methyl-8-(N-propyl-N-vinylaminomethyl)-1,6-dioxa-2-silacyclooctane,
2-ethoxy-2-methyl-8-(N-butyl-N-vinylaminomethyl)-1,6-dioxa-2-silacyclooctane,
2-ethoxy-2-methyl-8-(N-isopropyl-N-vinylaminomethyl)-1,6-dioxa-2-silacyclooctane,
2-ethoxy-2-methyl-8-(N-cyclohexyl-N-vinylaminomethyl)-1,6-dioxa-2-silacyclooctane,
2-ethoxy-2-methyl-8-(N,N-divinylaminomethyl)-1,6-dioxa-2-silacyclooctane,
2-ethoxy-2-methyl-8-(N-allyl-N-vinylaminomethyl)-1,6-dioxa-2-silacyclooctane,
2-ethoxy-2-methyl-8-(N-phenyl-N-vinylaminomethyl)-1,6-dioxa-2-silacyclooctane,
2-ethoxy-2-methyl-8-(N-benzyl-N-vinylaminomethyl)-1,6-dioxa-2-silacyclooctane,
2-ethoxy-2-methyl-8-(N-methyl-N-allylaminomethyl)-1,6-dioxa-2-silacyclooctane,
2-ethoxy-2-methyl-8-(N-ethyl-N-allylaminomethyl)-1,6-dioxa-2-silacyclooctane,
2-ethoxy-2-methyl-8-(N-propyl-N-allylaminomethyl)-1,6-dioxa-2-silacyclooctane,
2-ethoxy-2-methyl-8-(N-butyl-N-allylaminomethyl)-1,6-dioxa-2-silacyclooctane,
2-ethoxy-2-methyl-8-(N-isopropyl-N-allylaminomethyl)-1,6-dioxa-2-silacyclooctane,
2-ethoxy-2-methyl-8-(N-cyclohexyl-N-allylaminomethyl)-1,6-dioxa-2-silacyclooctane,
2-ethoxy-2-methyl-8-(N,N-diallylaminomethyl)-1,6-dioxa-2-silacyclooctane,
2-ethoxy-2-methyl-8-(N-phenyl-N-allylaminomethyl)-1,6-dioxa-2-silacyclooctane,
2-ethoxy-2-methyl-8-(N-benzyl-N-allylaminomethyl)-1,6-dioxa-2-silacyclooctane,
2-ethoxy-2-methyl-8-(N-methyl-N-phenylaminomethyl)-1,6-dioxa-2-silacyclooctane,
2-ethoxy-2-methyl-8-(N-ethyl-N-phenylaminomethyl)-1,6-dioxa-2-silacyclooctane,
2-ethoxy-2-methyl-8-(N-propyl-N-phenylaminomethyl)-1,6-dioxa-2-silacyclooctane,
2-ethoxy-2-methyl-8-(N-butyl-N-phenylaminomethyl)-1,6-dioxa-2-silacyclooctane,
2-ethoxy-2-methyl-8-(N-isopropyl-N-phenylaminomethyl)-1,6-dioxa-2-silacyclooctane,
2-ethoxy-2-methyl-8-(N-cyclohexyl-N-phenylaminomethyl)-1,6-dioxa-2-silacyclooctane,
2-ethoxy-2-methyl-8-(N,N-diphenylaminomethyl)-1,6-dioxa-2-silacyclooctane,
2-ethoxy-2-methyl-8-(N-allyl-N-phenylaminomethyl)-1,6-dioxa-2-silacyclooctane,
2-ethoxy-2-methyl-8-(N-benzyl-N-phenylaminomethyl)-1,6-dioxa-2-silacyclooctane,
2,2-dimethyl-8-(N-methyl-N-vinylaminomethyl)-1,6-dioxa-2-silacyclooctane,
2,2-dimethyl-8-(1-ethyl-N-vinylaminomethyl)-1,6-dioxa-2-silacyclooctane,
2,2-dimethyl-8-(N-propyl-N-vinylaminomethyl)-1,6-dioxa-2-silacyclooctane,
2,2-dimethyl-8-(N-butyl-N-vinylaminomethyl)-1,6-dioxa-2-silacyclooctane,
2,2-dimethyl-8-(N-isopropyl-N-vinylaminomethyl)-1,6-dioxa-2-silacyclooctane,
2,2-dimethyl-8-(N-cyclohexyl-N-vinylaminomethyl)-1,6-dioxa-2-silacyclooctane,
2,2-dimethyl-8-(N,N-divinylaminomethyl)-1,6-dioxa-2-silacyclooctane,
2,2-dimethyl-8-(N-allyl-N-vinylaminomethyl)-1,6-dioxa-2-silacyclooctane,
2,2-dimethyl-8-(N-phenyl-N-vinylaminomethyl)-1,6-dioxa-2-silacyclooctane,
2,2-dimethyl-8-(N-benzyl-N-vinylaminomethyl)-1,6-dioxa-2-silacyclooctane,
2,2-dimethyl-8-(N-methyl-N-allylaminomethyl)-1,6-dioxa-2-silacyclooctane,
2,2-dimethyl-8-(N-ethyl-N-allylaminomethyl)-1,6-dioxa-2-silacyclooctane,
2,2-dimethyl-8-(N-propyl-N-allylaminomethyl)-1,6-dioxa-2-silacyclooctane,
2,2-dimethyl-8-(N-butyl-N-allylaminomethyl)-1,6-dioxa-2-silacyclooctane,
2,2-dimethyl-8-(N-isopropyl-N-allylaminomethyl)-1,6-dioxa-2-silacyclooctane,
2,2-dimethyl-8-(N-cyclohexyl-N-allylaminomethyl)-1,6-dioxa-2-silacyclooctane,
2,2-dimethyl-8-(N,N-diallylaminomethyl)-1,6-dioxa-2-silacyclooctane,
2,2-dimethyl-8-(N-phenyl-N-allylaminomethyl)-1,6-dioxa-2-silacyclooctane,
2,2-dimethyl-8-(N-benzyl-N-allylaminomethyl)-1,6-dioxa-2-silacyclooctane,
2,2-dimethyl-8-(N-methyl-N-phenylaminomethyl)-1,6-dioxa-2-silacyclooctane,
2,2-dimethyl-8-(N-ethyl-N-phenylaminomethyl)-1,6-dioxa-2-silacyclooctane,
2,2-dimethyl-8-(N-propyl-N-phenylaminomethyl)-1,6-dioxa-2-silacyclooctane,
2,2-dimethyl-8-(N-butyl-N-phenylaminomethyl)-1,6-dioxa-2-silacyclooctane, 2,2-dimethyl-8-(N-isopropyl-N-phenylaminomethyl)-1,6-dioxa-2-silacyclooctane,
2,2-dimethyl-8-(N-cyclohexyl-N-phenylaminomethyl)-1,6-dioxa-2-silacyclooctane,
2,2-dimethyl-8-(N,N-diphenylaminomethyl)-1,6-dioxa-2-silacyclooctane,
2,2-dimethyl-8-(N-allyl-N-phenylaminomethyl)-1,6-dioxa-2-silacyclooctane, and
2,2-dimethyl-8-(N-benzyl-N-phenylaminomethyl)-1,6-dioxa-2-silacyclooctane.

These compounds are effective for improving compatibility with those resins having a solubility parameter at 25° C. of preferably at least 10 $(cal/cm^3)^{1/2}$, more preferably at least 11±1 $(cal/cm^3)^{1/2}$ (calculated according to Fedors equation).

Now the method for preparing the amino-containing organosilicon compound having formula (1) is described. In one embodiment, the amino-containing organosilicon compound of formula (1) is prepared by reacting an amine compound with a γ-glycidoxypropylalkoxysilane and subjecting the resulting reaction mixture to dealcoholization cyclization under solvent reflux. The amine compound has the general formula (2):

(2)

wherein $R^1$ is a substituted or unsubstituted, $C_1$-$C_{10}$ alkyl, $C_2$-$C_{10}$ alkenyl, $C_6$-$C_{10}$ aryl or $C_7$-$C_{10}$ aralkyl group. $R^2$ is a substituted or unsubstituted, $C_2$-$C_{10}$ alkenyl, $C_6$-$C_{10}$ aryl or $C_7$-$C_{10}$ aralkyl group. The γ-glycidoxypropylalkoxysilane has the general formula (3):

(3)

wherein $R^3$ and $R^4$ are each independently a substituted or unsubstituted, $C_1$-$C_{10}$ monovalent hydrocarbon group, and n is an integer of 0 to 2.

Examples of the compound having formula (2) include methylvinylamine, ethylvinylamine, n-propylvinylamine, n-butylvinylamine, isopropylvinylamine, cyclohexylvinylamine, divinylamine, allylvinylamine, phenylvinylamine, benzylvinylamine, methylallylamine, ethylallylamine, n-propylallylamine, n-butylallylamine, isopropylallylamine, cyclohexylallylamine, diallylamine, phenylallylamine, benzylallylamine, methylphenylamine, ethylphenylamine, n-propylphenylamine, n-butylphenylamine, isopropylphenylamine, cyclohexylphenylamine, vinylphenylamine, allylphenylamine, diphenylamine, and benzylphenylamine.

Examples of the compound having formula (3) include γ-glycidoxypropyltrimethoxysilane, γ-glycidoxypropylmethyldimethoxysilane, γ-glycidoxypropyldimethylmethoxysilane, γ-glycidoxypropyltriethoxysilane, γ-glycidoxypropylmethyldiethoxysilane, and γ-glycidoxypropyldimethylethoxysilane.

When the amine compound of formula (2) is reacted with the γ-glycidoxypropylalkoxysilane compound of formula (3), they may be combined in any desired ratio. It is preferred from the aspects of reactivity and productivity that 0.5 to 10 moles, more preferably 0.5 to 5 moles, and even more preferably 0.8 to 5 moles of the amine compound of formula (2) be used per mole of the silane compound of formula (3).

The reaction temperature is typically in a range of 50° C. to 200° C., preferably 70° C. to 200° C., and more preferably 80° C. to 160° C. though not limited thereto. The reaction time is typically 1 to 20 hours, preferably 1 to 15 hours.

Although the reaction may take place in a solventless system, a solvent may be used. Suitable solvents include hydrocarbon solvents such as pentane, hexane, cyclohexane, heptane, isooctane, benzene, toluene and xylene, alcohol solvents such as methanol and ethanol, ether solvents such as diethyl ether, tetrahydrofuran and dioxane, ester solvents such as ethyl acetate and butyl acetate, aprotic polar solvents such as acetonitrile and N,N-dimethylformamide, and chlorinated hydrocarbon solvents such as dichloromethane and chloroform. These solvents may be used alone or in admixture of two or more. When the solvent is used, the reaction is preferably performed under solvent reflux for preventing intermolecular condensation.

In the subsequent step of subjecting the reaction mixture resulting from reaction of the amine compound of formula (2) with the γ-glycidoxypropylalkoxysilane of formula (3) to dealcoholization cyclization under solvent reflux, a solvent may be used. Suitable solvents include hydrocarbon solvents such as pentane, hexane, cyclohexane, heptane, isooctane, benzene, toluene and xylene, ether solvents such as diethyl ether, tetrahydrofuran and dioxane, ester solvents such as ethyl acetate and butyl acetate, aprotic polar solvents such as acetonitrile and N,N-dimethylformamide, chlorinated hydrocarbon solvents such as dichloromethane and chloroform, and amine compounds of formula (2). These solvents may be used alone or in admixture of two or more. Preferred are those solvents having a boiling point higher than that of alcohol generated during the reaction. The alcohol generated during the reaction is preferably distilled off from the reactor as gas or condensed liquid. On distillation of alcohol, it is recommended to distill off the solvent (used for the reaction) together because this facilitates alcohol removal. It is also recommended that the solvent is separated from the distilled fraction and recycled to the reactor, because the amount of the solvent used is reduced.

In an alternative embodiment, the amino-containing organosilicon compound of formula (1) may be prepared by simultaneously effecting reaction of an amine compound of formula (2) with a γ-glycidoxypropylalkoxysilane of formula (3) and dealcoholization cyclization under solvent reflux. This embodiment is advantageous in terms of yield.

Although the dealcoholization cyclization reaction may take place in the absence of a catalyst, a catalyst may be used. Examples of the catalyst used include acidic, basic, and transition metal catalysts, with the basic catalysts being preferred for reactivity. Suitable basic catalysts include alkali metal hydroxides, alkaline earth metal hydroxides, alkali metal alkoxides, and alkaline earth metal alkoxides, and quaternary ammonium hydroxides. Illustrative examples include alkali metal hydroxides such as potassium hydroxide, sodium hydroxide and cesium hydroxide, alkali metal alkoxides such as potassium methoxide, sodium methoxide, potassium ethoxide and sodium ethoxide, and alkyl- or aryl-containing quaternary ammonium hydroxides such as tetramethylammonium hydroxide, tetraethylammonium hydroxide, tetrapropylammonium hydroxide, tetrabutylammonium hydroxide and trimethylbenzylammonium hydroxide. Inter alia, alkali metal alkoxides are preferred. The basic catalyst may be used as an aqueous solution or alcohol solution.

These catalysts may be used alone or in admixture of two or more. The amount of the catalyst used is not particularly limited. The catalyst is preferably used in an amount of 0.001 to 1.0 mole, more preferably 0.005 to 0.1 mole per mole of silicon atom. Too small amounts of the catalyst may fail to exert its effect. With too large amounts of the catalyst, a reaction promoting effect commensurate to the extra amount may not be obtained.

The organosilicon compound of the invention may be used as such, but preferably diluted with a suitable solvent prior to use for ease of handling. Suitable solvents include water, alcohol solvents such as methanol and ethanol, hydrocarbon solvents such as pentane, hexane, cyclohexane, heptane, isooctane, benzene, toluene and xylene, ketone solvents such as acetone and methyl isobutyl ketone, ether solvents such as diethyl ether, tetrahydrofuran and dioxane, ester solvents such as ethyl acetate and butyl acetate, aprotic polar solvents such as acetonitrile and N,N-dimethylformamide, and chlorinated hydrocarbon solvents such as dichloromethane and chloroform, with water and alcohols being preferred. The solvent is preferably used in such amounts as to dilute the organosilicon compound in a concentration of 0.001 to 50% by weight.

At least one additive selected from pigments, defoamers, lubricants, antiseptics, pH control agents, film formers, antistatic agents, anti-fungus agents, surfactants, dyes and the like may be added to the organosilicon compound as long as the benefits of the invention are not impaired.

The organosilicon compound can be used in any desired applications. Typical applications include, but are not limited to, surface treatment of inorganic fillers, liquid sealants, treatment of casting molds, surface modification of resins, polymer modifiers, and additives to aqueous coating compositions.

The organosilicon compound may be used for surface treatment of inorganic fillers such as glass fibers, powder silica, powder alumina, powder talc and powder calcium carbonate. The glass fibers may be made of common type glass, for example, E glass or C glass. The glass fibers used herein are not limited in product form. Various glass fiber products are available, for example, bundles, twisted yarns, and woven fabrics of glass filaments having a diameter of 3 to 30 μm.

Treatment of an inorganic filler with the organosilicon compound as a surface treating agent may be carried out by standard techniques, for example, a technique of immersing the filler in the organosilicon compound or a dilution thereof, taking out the filler, and drying, or a technique of spraying the organosilicon compound or a dilution thereof to the surface of the filler and drying.

EXAMPLE

Examples of the invention are given below by way of illustration and not by way of limitation. Me stands for methyl and Et for ethyl.

Example 1

Preparation of 2,2-dimethoxy-8-(N,N-diallylaminomethyl)-1,6-dioxa-2-silacyclooctane A flask equipped with a stirrer, reflux condenser, dropping funnel and thermometer was charged with 47 g (0.48 mol) of diallylamine. To the flask, 94 g (0.40 mol) of γ-glycidoxypropyltrimethoxysilane was added dropwise at a temperature of 105-115° C. over 6 hours. Stirring was continued for 2 hours at the temperature, obtaining a yellow clear reaction solution.

A flask equipped with a stirrer, fractionating head, reflux condenser, dropping funnel and thermometer was charged with 300 ml of toluene and 1.5 g of 28 wt % methanol solution of sodium methoxide. The reaction solution was added dropwise to the toluene under reflux, while an alcohol-containing fraction was gradually removed. Fractional distillation was continued until the internal temperature reached 145° C. At this point, the reaction was completed. The reaction solution was distilled, collecting 92 g of a pale yellow clear fraction at 139-141° C./0.3 kPa.

Figure 1:
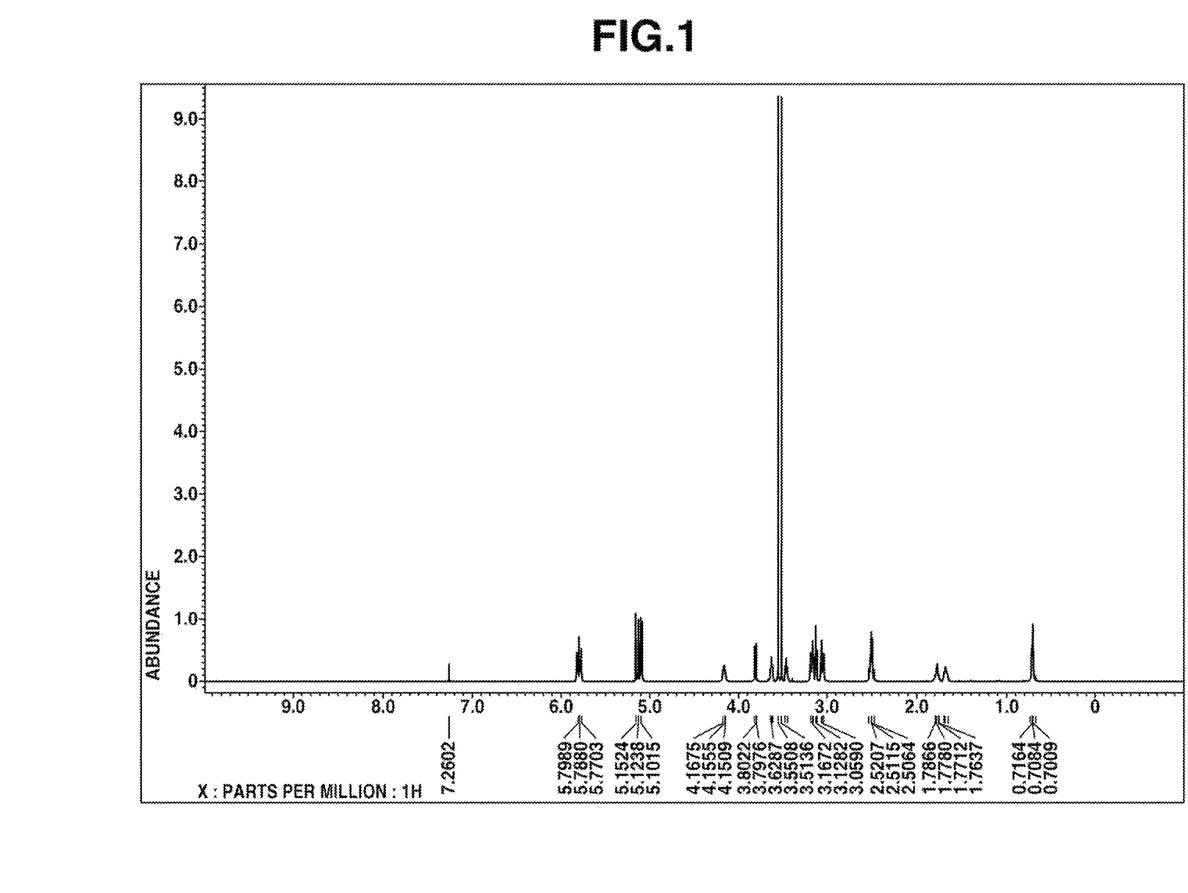
FIG. 1 is a diagram showing a $^1$H-NMR spectrum in deuterated chloroform of the compound in Example 1.
Figure 2:
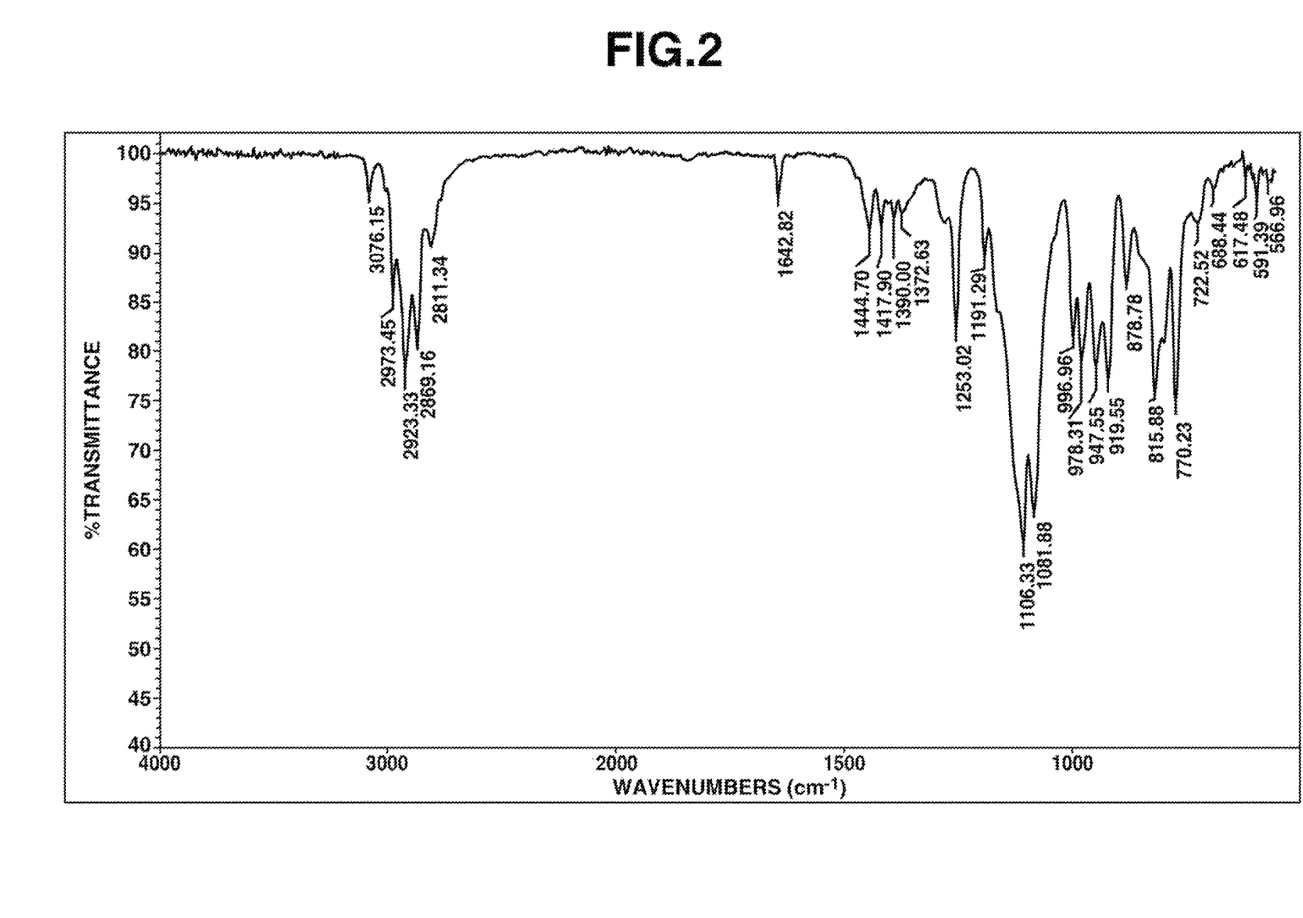
FIG. 2 is a diagram showing an IR spectrum of the compound in Example 1.

This fraction was analyzed by mass, $^1$H-NMR and IR spectroscopy.

Mass spectrum: m/z 301, 260, 228, 110, 41
$^1$H-NMR spectrum (in deuterated chloroform): FIG. 1
IR spectrum: FIG. 2

From these data, the fraction was identified to be 2,2-dimethoxy-8-(N,N-diallylaminomethyl)-1,6-dioxa-2-silacyclooctane.

Example 2

Preparation of 2,2-dimethoxy-8-(N-methyl-N-phenylamino-methyl)-1,6-dioxa-2-silacyclooctane A flask equipped with a stirrer, reflux condenser, dropping funnel and thermometer was charged with 96 g (0.90 mol) of methylaniline. To the flask, 71 g (0.30 mol) of γ-glycidoxypropyltrimethoxysilane was added dropwise at a temperature of 125-130° C. over 6 hours. Stirring was continued for 2 hours at the temperature, obtaining a yellow clear reaction solution.

A flask equipped with a stirrer, fractionating head, reflux condenser, dropping funnel and thermometer was charged with 200 ml of toluene and 0.5 g of 28 wt % methanol solution of sodium methoxide. The reaction solution was added dropwise to the toluene under reflux, while an alcohol-containing fraction was gradually removed. Fractional distillation was continued until the internal temperature reached 145° C. At this point, the reaction was completed. The reaction solution was distilled, collecting 68 g of a pale yellow clear fraction at 157-158° C./0.2 kPa.

Figure 3:
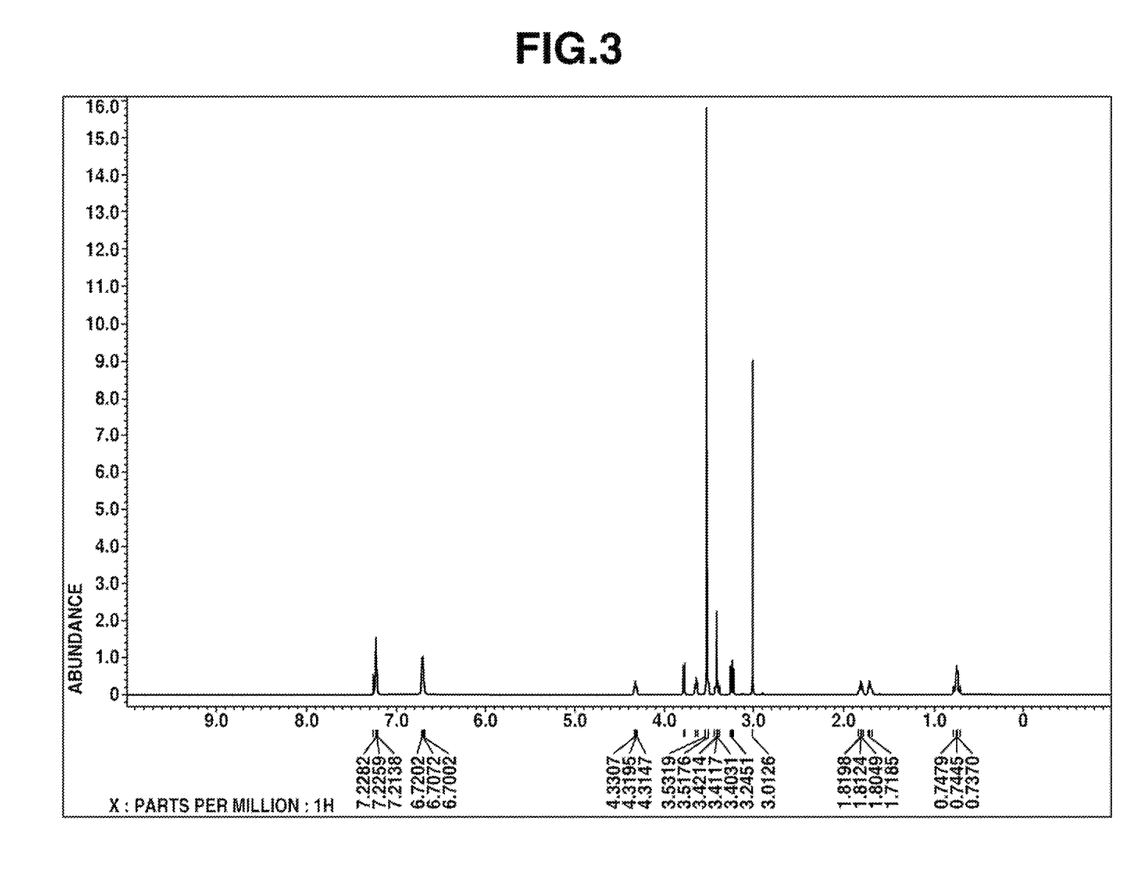
FIG. 3 is a diagram showing a $^1$H-NMR spectrum in deuterated chloroform of the compound in Example 2.
Figure 4:
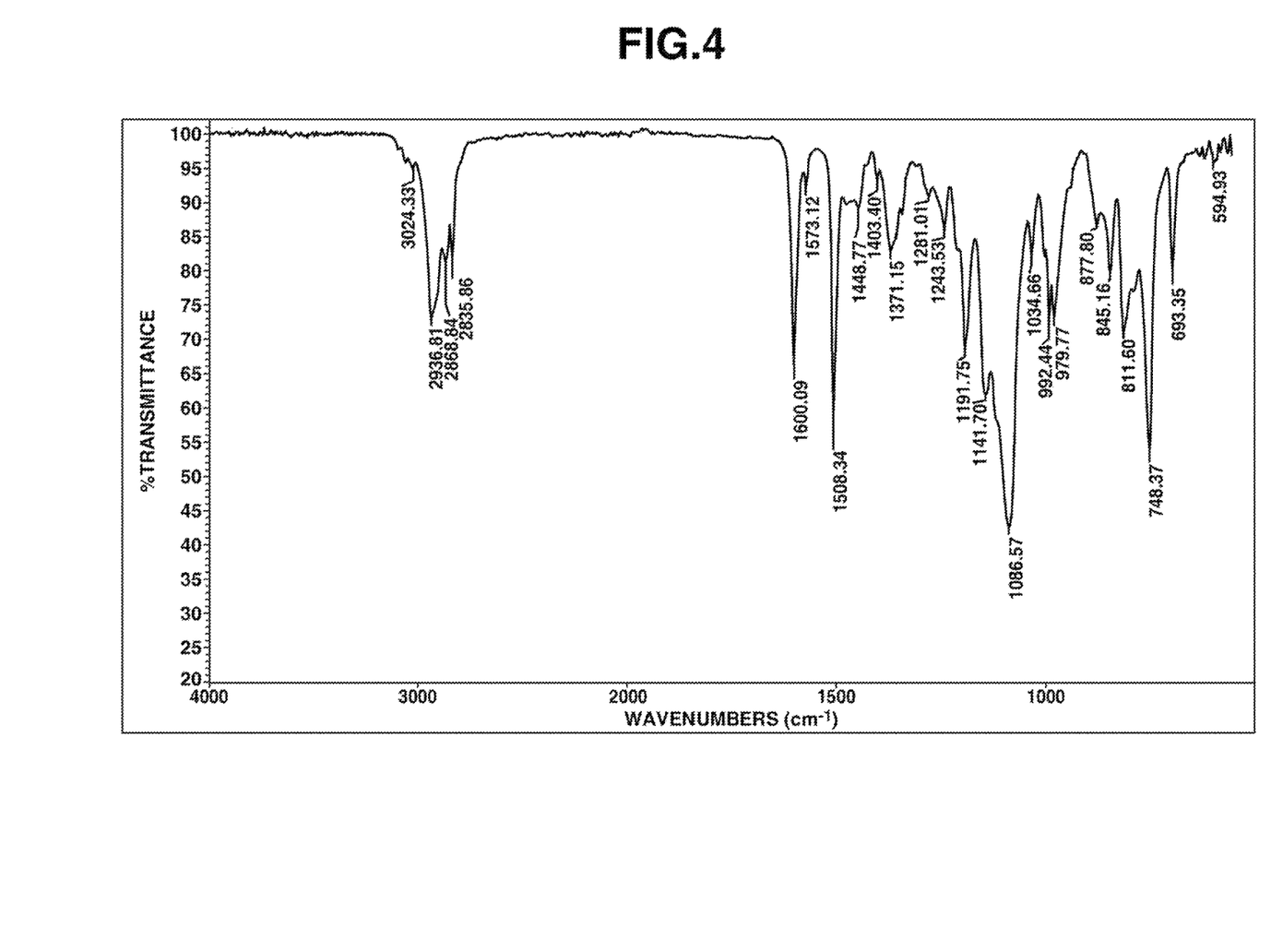
FIG. 4 is a diagram showing an IR spectrum of the compound in Example 2.

This fraction was analyzed by mass, $^1$H-NMR and IR spectroscopy.

Mass spectrum: m/z 311, 280, 191, 120, 77
$^1$H-NMR spectrum (in deuterated chloroform): FIG. 3
IR spectrum: FIG. 4

From these data, the fraction was identified to be 2,2-dimethoxy-8-(N-methyl-N-phenylaminomethyl)-1,6-dioxa-2-silacyclooctane.

Example 3

Preparation of 2-ethoxy-2-methyl-8-(N,N-diallylamino-methyl)-1,6-dioxa-2-silacyclooctane A flask equipped with a stirrer, fractionating head, reflux condenser, dropping funnel and thermometer was charged with 190 g (2.0 mol) of diallylamine and 0.5 g of 20 wt % ethanol solution of sodium ethoxide. To the flask, 74 g (0.30 mol) of γ-glycidoxypropyldiethoxymethylsilane was added dropwise over 8 hours under reflux, while a fraction containing ethanol generated was gradually removed. The reaction solution was distilled, collecting 52 g of a yellow clear fraction at 121-122° C./0.2 kPa.

Figure 5:
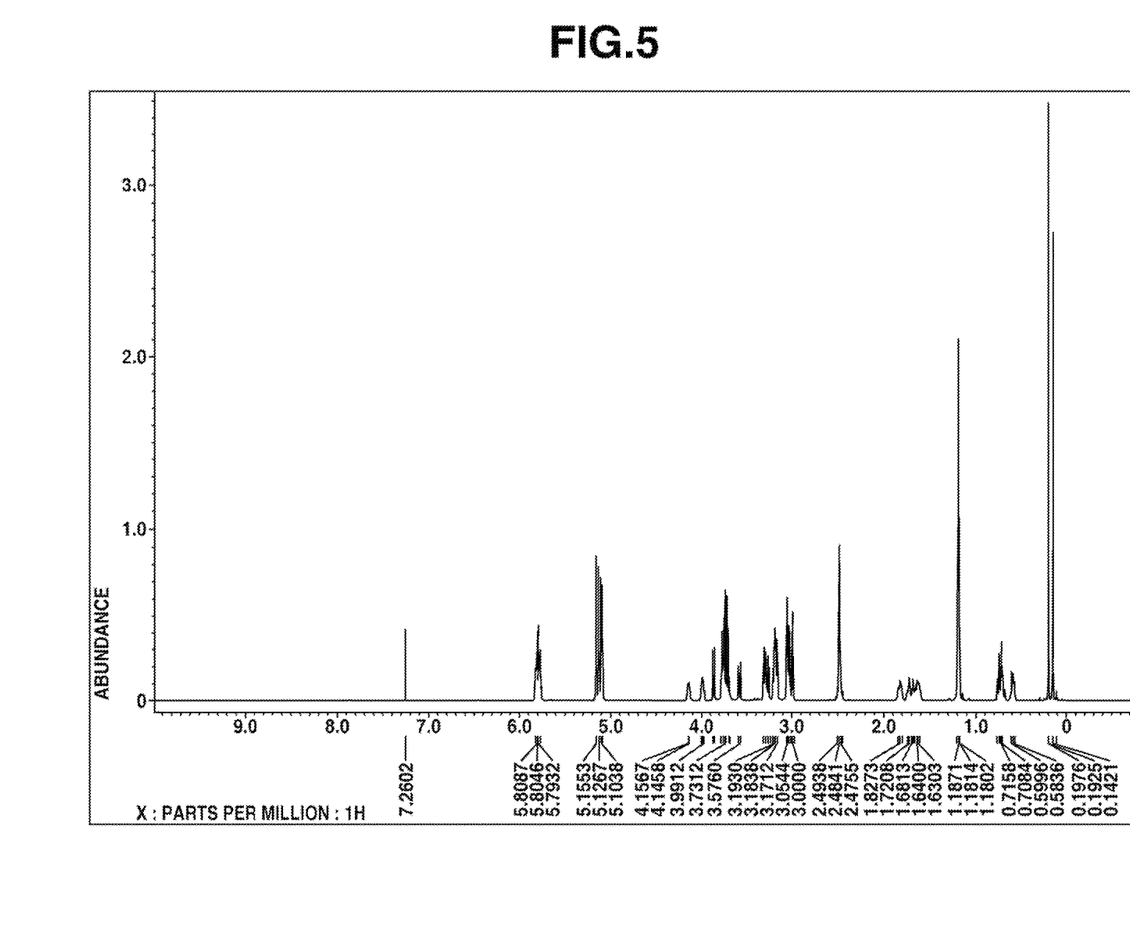
FIG. 5 is a diagram showing a $^1$H-NMR spectrum in deuterated chloroform of the compound in Example 3.
Figure 6:
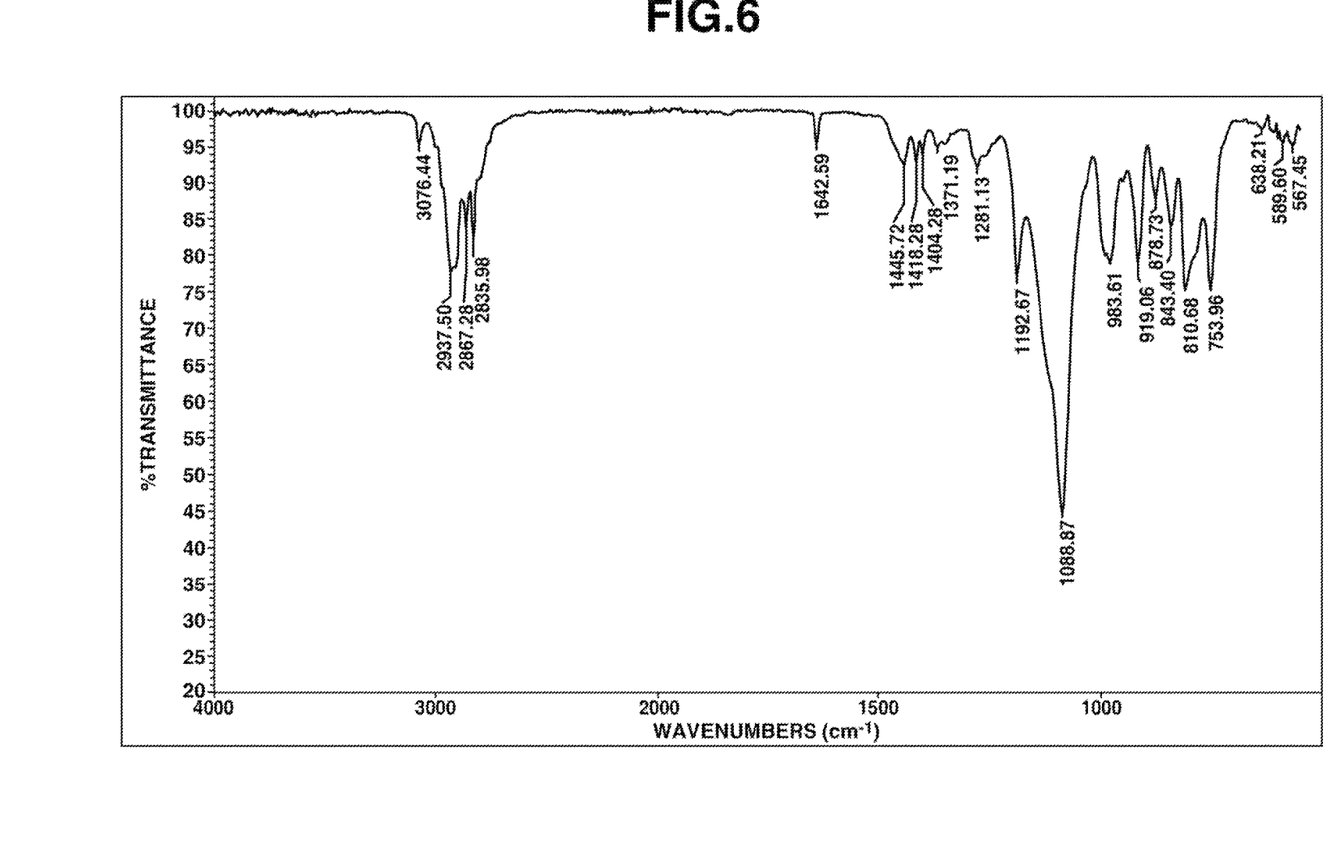
FIG. 6 is a diagram showing an IR spectrum of the compound in Example 3.

This fraction was analyzed by mass, $^1$H-NMR and IR spectroscopy.

Mass spectrum: m/z 299, 284, 258, 110, 41

$^1$H-NMR spectrum (in deuterated chloroform): FIG. 5

IR spectrum: FIG. 6

From these data, the fraction was identified to be 2-ethoxy-2-methyl-8-(N,N-diallylaminomethyl)-1,6-dioxa-2-silacyclooctane.

Japanese Patent Application No. 2015-134132 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An amino-containing organosilicon compound having the general formula (1):

(1)

wherein
$R^1$ is an unsubstituted $C_1$-$C_{10}$ alkyl or $C_2$-$C_{10}$ alkenyl group,
$R^2$ is an unsubstituted $C_2$-$C_{10}$ alkenyl or $C_6$-$C_{10}$ aryl group,
$R^3$ and $R^4$ are each independently an unsubstituted $C_1$-$C_{10}$ alkyl group, and
n is an integer of 0 to 2.

2. A method for preparing the amino-containing organosilicon compound of claim 1, comprising the steps of
reacting an amine compound with a γ-glycidoxypropylalkoxysilane, and subjecting the resulting reaction mixture to dealcoholization cyclization under solvent reflux,
the amine compound having the general formula (2):

(2)

wherein $R^1$ is an unsubstituted $C_1$-$C_{10}$ alkyl or $C_2$-$C_{10}$ alkenyl group and $R^2$ is an unsubstituted $C_2$-$C_{10}$ alkenyl or $C_6$-$C_{10}$ aryl group, and the γ-glycidoxypropylalkoxysilane having the general formula (3):

(3)

wherein $R^3$ and $R^4$ are each independently an unsubstituted $C_1$-$C_{10}$ alkyl group, and n is an integer of 0 to 2.

3. A method for preparing the amino-containing organosilicon compound of claim 1, comprising the step of
reacting an amine compound with a γ-glycidoxypropylalkoxysilane while simultaneously effecting dealcoholization cyclization under solvent reflux,
the amine compound having the general formula (2):

$$\underset{R^2}{\overset{R^1}{\underset{|}{\diagdown}}}NH \qquad (2)$$

wherein $R^1$ is an unsubstituted $C_1$-$C_{10}$ alkyl or $C_2$-$C_{10}$ alkenyl group and $R^2$ is an unsubstituted $C_2$-$C_{10}$ alkenyl or $C_6$-$C_{10}$ aryl group, and the γ-glycidoxypropylalkoxysilane having the general formula (3):

(3)

wherein $R^3$ and $R^4$ are each independently an unsubstituted $C_1$-$C_{10}$ alkyl group, and n is an integer of 0 to 2.

4. The method of claim 2 wherein the dealcoholization cyclization is effected in the presence of a basic catalyst.

5. The method of claim 3 wherein the dealcoholization cyclization is effected in the presence of a basic catalyst.

6. The amino-containing organosilicon compound of claim 1, wherein $R^1$ is vinyl or allyl, $R^2$ is vinyl, allyl, or phenyl, and $R^3$ and $R^4$ are independently methyl or ethyl.

7. The amino-containing organosilicon compound of claim 1, which is:
2,2-dimethoxy-8-(N,N-diallylaminomethyl)-1,6-dioxa-2-silacyclooctane;
2,2-dimethoxy-8-(N-methyl-N-phenylaminomethyl)-1,6-dioxa-2-silacyclooctane; or
2-ethoxy-2-methyl-8-(N,N-diallylaminomethyl)-1,6-dioxa-2-silacyclooctane.

* * * * *